United States Patent
Brack et al.

(10) Patent No.: US 6,755,864 B1
(45) Date of Patent: Jun. 29, 2004

(54) TIBIA PART FOR A KNEE JOINT PROSTHESIS AND A KIT WITH A TIBIA PART OF THIS KIND

(75) Inventors: René Brack, Cham (CH); Roger Scherrer, Schaffhausen (CH); Vincent Leclercq, Winterthur (CH)

(73) Assignee: Sulzer Orthopedics Ltd., Baar (CH)

( * ) Notice: Subject to any disclaimer, the term of this patent is extended or adjusted under 35 U.S.C. 154(b) by 0 days.

(21) Appl. No.: 09/667,950

(22) Filed: Sep. 22, 2000

(30) Foreign Application Priority Data

Sep. 24, 1999 (EP) .......................................... 99810862

(51) Int. Cl.[7] .................................................. A61F 2/38
(52) U.S. Cl. .................................. 623/20.29; 623/20.15
(58) Field of Search .......................... 623/20.14, 20.15, 623/20.27, 20.28, 20.29, 20.3, 20.32, 20.33, 20.34, 20.35

(56) References Cited

FOREIGN PATENT DOCUMENTS

| EP | 0 519 873 A2 | 12/1992 |
| EP | 0 904 749 A2 | 3/1999 |
| EP | 0 913 132 A1 | 5/1999 |

*Primary Examiner*—David J. Isabella
(74) *Attorney, Agent, or Firm*—Townsend and Townsend and Crew LLP

(57) ABSTRACT

A tibia part for a knee joint prosthesis. The prosthesis includes a tibia bearing surface for the support of a bearing body and a bore for the reception of a guiding element. A cut-out for the rear cruciate ligament is provided in the tibia bearing surface and the bore is formed in such a manner that it can, depending on the design of the guiding element, receive the latter either rotationally fixedly relative to the tibia part or rotatably relative to the tibia part.

11 Claims, 14 Drawing Sheets

Fig. 8
Fig. 9
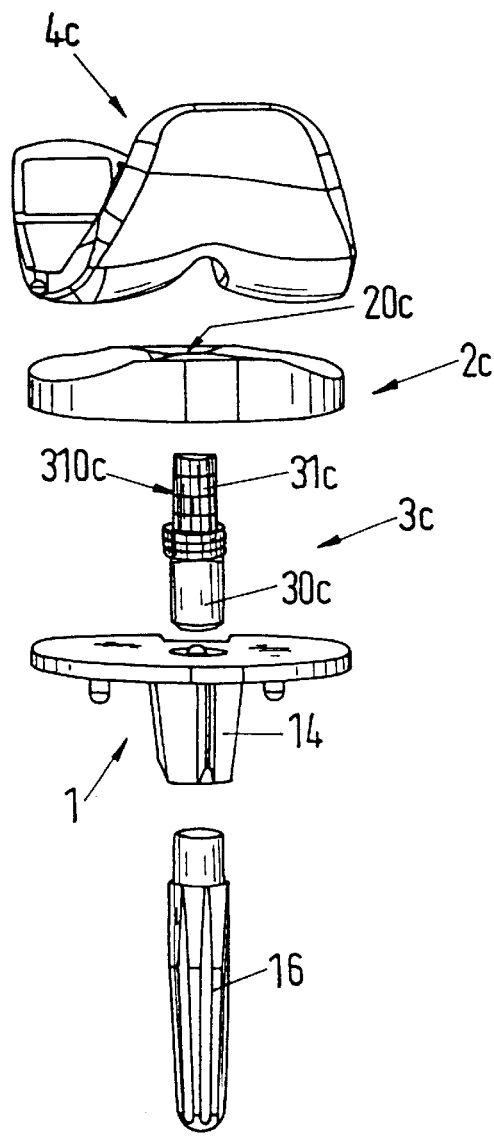
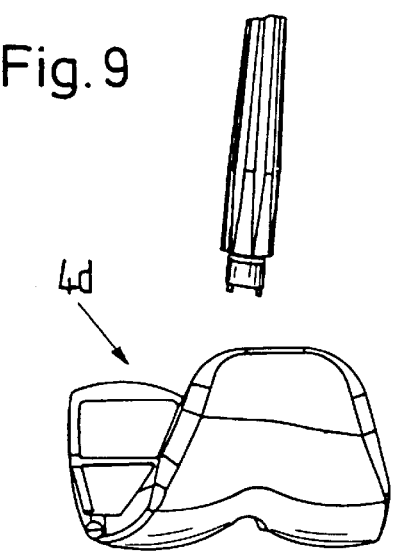
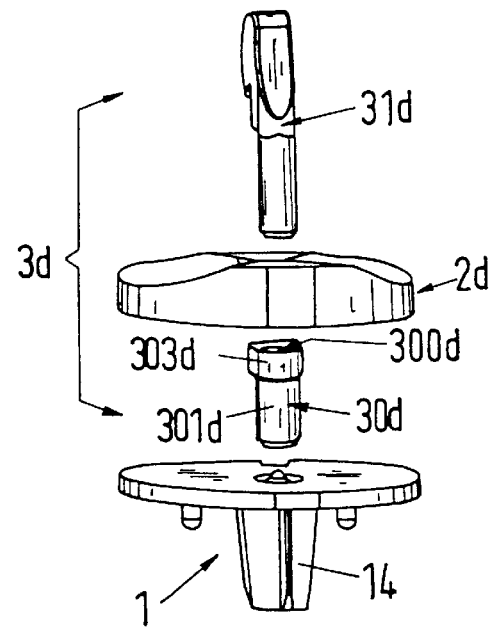
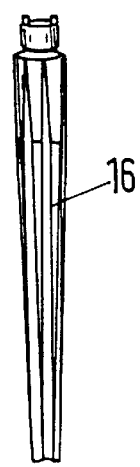

TIBIA PART FOR A KNEE JOINT PROSTHESIS AND A KIT WITH A TIBIA PART OF THIS KIND

BACKGROUND OF THE INVENTION

The invention relates to a tibia part for a knee joint prosthesis and to a kit for putting together a knee joint prosthesis. Furthermore, the invention relates to a method for implanting and for re-operating a knee joint prosthesis.

Knee joint prostheses usually comprise a tibia part, which is fixed in the tibia, a femur part, which is fixed in the femur, as well as a bearing body which is arranged between them and which is often designated as a meniscus part. The tibia part has a tibia bearing surface for the support of the bearing body. The bearing body is provided on its side which faces away from the tibia bearing surface—that is, on the side facing the femur—with bearing shells which cooperate with condyles (running surfaces) of the femur part.

Nowadays knee joint prostheses are available in a large number of different prosthesis types, the functioning principles of which often differ strongly from one another. This is connected, among other things, with the fact that the prosthesis, depending on the state of the ligaments (cruciate ligaments, collateral ligaments), must wholly or partly take over the various functions of the ligaments in the respective patient.

Thus for example types of prostheses are known (see e.g. EP-A-0,923,916) in which the meniscus part is fixed to the tibia bearing surface of the tibia part, so that the meniscus part is arranged to be immobile relative to the tibia part.

Furthermore, prosthesis types are known in which the meniscus part is journalled on the tibia bearing surface so as to be movable relative to the tibia part, i.e. is thus either slidingly displaceable on the tibia bearing surface or is rotatable on the tibia bearing surface or both.

In EP-A-0,913,132 for example a knee joint prosthesis is shown in which the meniscus part is admittedly slidingly displaceable, but is however substantially rotationally fixedly seated on the tibia bearing surface of the tibia part, so that the meniscus part is admittedly displaceable on the tibia bearing surface in the anterior/posterior direction relative to the tibia part, but is substantially not rotatable.

Furthermore, prosthesis types are known in which the meniscus part is admittedly rotatable, but however not displaceably journalled on the tibia part relative to the tibia bearing surface, so that the meniscus part is only rotatable relative to the tibia part, but cannot be displaced.

Finally, prosthesis types are known from EP-A-0,519,873 in which the meniscus part is both slidingly displaceable and rotatable relative to the tibia bearing surface.

Moreover, prosthesis types are known in which means are provided in order to stabilize the femur part during the flexion (bending) in the posterior position relative to the meniscus part or relative to the tibia part respectively. This prosthesis type is used in particular when the rear cruciate ligament is no longer present or is no longer capable of functioning.

In particular in cases in which the collateral ligaments are no longer present or are no longer sufficiently capable of functioning, prosthesis types are used in which means for the lateral stabilizing (varus/valgus stabilizing) are provided.

From this non-exhaustive listing it is already clear that a large number of different embodiments of the individual components of a knee joint prosthesis, in particular also a large number of different tibia parts, must be provided in order that the respective prosthesis which is ideal for the respective patient can be put together.

For each prosthesis type there exists a tibia part which is specially matched to this type in order to ensure as good a cooperation with the remaining components of the prosthesis as possible. This means: A tibia part which was manufactured for a specific prosthesis type cannot as a rule be used for other prosthesis types. As a result of this there exist in part considerable constructional differences between tibia parts which belong to different prosthesis types.

This is however disadvantageous in particular from the point of view of the manufacturing technology, since for each prosthesis type the tibia part must be produced in accordance with a manufacturing process which is specific to the respective tibia part. Thus in order to provide a plurality of tibia parts for different prosthesis types, a plurality of partly very different, manufacturing processes must also be used, which is very complicated from the technical side and in addition is also economically disadvantageous.

If a kit is to be created by means of which different prosthesis types can be put together, then this kit must comprise a large number of tibia parts which differ from one another in regard to their functional design. Since in addition for each prosthesis type a plurality of tibia parts of different sizes must yet also be present in the kit in order to take into account the different anatomical circumstances of the patients, a kit of this kind necessarily comprises a very large number of individual components.

Here the invention wishes to provide a remedy. It is therefore an object of the invention to propose a tibia part which considerably simplifies the manufacture for different prosthesis types. Furthermore, through the tibia part a kit for the putting together of a knee joint prosthesis should be enabled which comprises considerably fewer different tibia parts without concessions therefore being necessary on the flexibility with respect to the different prosthesis types which can be realized with the kit or concessions on the functioning of the knee joint prosthesis.

SUMMARY OF THE INVENTION

In accordance with the invention thus a tibia part for a knee joint prosthesis is proposed which comprises a tibia bearing surface for the support of a bearing body (meniscus part) and a bore for the reception of a guiding element, with a cut-out for the rear cruciate ligament being provided in the tibia bearing surface and with the bore being formed in such a manner that it can, depending on the design of the guiding element, receive the latter either rotationally fixedly relative to the tibia part or rotatably relative to the tibia part.

These measures enable a tibia part which is suitable for a plurality of functionally different prosthesis types, which means that the same tibia part can be combined with different bearing bodies and/or femur parts and/or guiding elements in order thus to be able to put together different prosthesis types. Through the cut-out for the reception of the rear cruciate ligament the tibia part is suitable for prosthesis types in which the rear cruciate ligament remains intact and is capable of functioning. Through the design of the bore in the tibia bearing surface the tibia part in accordance with the invention is suitable both for prosthesis types in which the bearing body is rotationally fixedly seated relative to the tibia part and for prosthesis types in which the bearing body is rotatably journalled on the tibia bearing surface.

The variability of the tibia part in accordance with the invention or, respectively, its compatibility with different prosthesis types means a considerable simplification of the manufacturing process, since the same tibia part can be used for different prosthesis types.

The tibia part is preferably provided with an extension piece which serves for securing the tibia part in the tibia, with means being provided in order to connect the extension piece firmly to a separate anchoring shaft in the event that a separate anchoring shaft appears indicated as a result of the anatomical circumstances. Through this it is possible to provide the tibia part with differently designed anchoring shafts, in particular anchoring shafts of different lengths (insofar as indicated), in order thus to be able to match the anchoring of the tibia part in the tibia ideally to the special application.

In accordance with a first exemplary embodiment, securing means are provided at the tibia part in order to fix the bearing body on the tibia bearing surface. This exemplary embodiment is suitable in particular for prosthesis types in which the bearing body is immobile relative to the tibia part.

In a second exemplary embodiment these securing means are not provided, so that the bearing body is movably journalled on the tibia bearing surface relative to the tibia part.

In regard to a manufacturing process which is as simple as possible, it is advantageous when these two exemplary embodiments differ only through the securing means and are otherwise practically the same constructionally.

In accordance with a further aspect of the invention a kit for putting together a knee joint prosthesis is proposed. The kit comprises at least one tibia part having a tibia bearing surface and further comprises at least one bearing body which can be journalled on the tibia bearing surface and which has bearing shells on its side which faces away from the tibia bearing surface, as well as at least one femur part having condyles for cooperating with the bearing shells of the bearing body. The tibia part of this kit is formed as a tibia part in accordance with the invention, as has already been described above.

Since the tibia part in accordance with the invention is suitable for a plurality of functionally different prosthesis types, it is not necessary in a kit of this kind to provide a tibia part for every prosthesis type which is specially matched to this prosthesis type. Rather, the same tibia part can be combined with functionally different or functionally differently cooperating components (e.g. bearing bodies, femur parts, guiding elements) respectively without Concessions as regards the capability of functioning of the knee joint prosthesis being necessary for this. Through this, considerably fewer different tibia parts are required for the kit without the flexibility of the kit thereby being diminished in regard to the prosthesis types which can be put together. This represents a considerable simplification not only in relation to the number of the tibia parts which are contained in a kit, but also in the manufacturing technology.

In the kit preferably at least one tibia part and at least one bearing body are preferably formed in such a manner that the bearing body can be fixed to the tibia bearing surface in order that prosthesis types with a bearing body which is fixed relative to the tibia part can also be realized.

In order to realize prosthesis types with bearing bodies which are both displaceable and rotatable relative to the tibia part, the kit preferably comprises at least one bearing body which can be slidingly displaceably journalled on the tibia bearing surface and at least one guiding element which is designed as a connecting rod, the one end of which can be rotatably journalled in the bore of the tibia part and which has a guiding section which is formed and cooperates with the bearing body in such a manner that the bearing body is displaceable relative to the tibia bearing surface in the anterior/posterior direction.

For prosthesis types with a rotatably—but not displaceably—journalled bearing body at least one bearing body is preferably provided in the kit which has on its side facing the tibia bearing surface a molded on or fixed guiding element by means of which the bearing body can be rotatably journalled in the bore of the tibia part.

For prosthesis types with posterior stabilizing the kit preferably comprises at least one bearing body which has an axially through-going elongate hole and at least one guiding element which passes through the elongate hole of the bearing body, with the one end of the guiding element being formed as a pin which extends into the bore in the tibia part and is there rotatably journalled, and the other end protruding in between the condyles of the femur part and having a guiding surface for cooperating with a stabilizing element which is provided in the femur part.

Furthermore, for the cases in which the rear cruciate ligament and the collateral ligaments no longer exist or are no longer capable of functioning it is advantageous when the kit has at least one guiding element with a guiding piece and a coupling piece, with the guiding piece being designed in such a manner that it can be arranged both rotationally fixedly relative to the tibia part in the bore of the tibia part and can also be rotationally fixedly connected to the bearing body. The coupling piece is rotatably journalled in the guiding piece and has a stabilizing piece which reaches between the condyles of the femur part in order to cooperate there with a stabilizing element. With this, posteriorly stabilized prosthesis types with additional varus/valgus stabilization (when collateral ligaments which are capable of functioning are absent) can be realized.

The stabilizing, element at the femur part comprises in an advantageous variant embodiment a connection web which is formed in the manner of a wall and which together with two side walls forms a box which is arranged between the two condyles of the femur part and which cooperates with the guiding surface of the guiding element or with the stabilizing piece of the coupling piece of the guiding element respectively. Depending on which type of knee joint prosthesis the connection web which is formed in the manner of a wall cooperates with, during the flexion either the outer wall of the connection web which is formed in the manner of a wall enters into contact with the guiding surface of the guiding element, or else the inner wall of the connection web which is formed in the manner of a wall enters into contact with the guiding surface of the coupling piece of the guiding element. Moreover, in the last named variant a varus/valgus stabilizing also takes place with the help of the stabilizing piece, which reaches between the condyles of the femur part, and the side surfaces (stabilizing surfaces) of which cooperate with the side walls of the box.

In a preferred exemplary embodiment the kit in accordance with the invention comprises all the above-listed elements. A kit of this kind is distinguished by its extremely high degree of flexibility, which means that dependently of the respective indication the different prosthesis types can be put together in a modular manner from this kit. A particular advantage in this is that this flexibility is also intra-operatively present, which means that in cases in which he finds special anatomical conditions during an operation in spite of careful pre-operational planning, the orthopedist can still select that prosthesis type from the kit which is best suited for the respective application and put it together during the operation. This high degree of flexibility is advantageous in particular because e.g. the state of the ligaments cannot always be determined with absolute certainty in spite of careful pre-operational planning or else the bone material is actually in a better or worse condition than the pre-operational analysis indicates, so that a prosthesis type which is different from the originally pre-operationally planned prosthesis type appears to be indicated instead.

Since the tibia part in accordance with the invention can be combined in a modular manner with the other components of the kit to form a plurality of functionally different prosthesis types, the number of the tibia parts in the kit can be kept relatively low. At most four tibia parts of different kinds are preferably present in the mentioned preferred exemplary embodiment of the kit, namely two for cemented and two for cementless knee joint prostheses, with in both cases—cemented and cementless—in each case one tibia part being provided for fixed bearing bodies and one for mobile bearing bodies. The tibia parts which are provided for cemented prostheses on the one hand and for cementless prostheses on the other hand do not differ in their geometrical design. The tibia parts for cemented prostheses have cement pockets at their lower side facing the tibia. In the tibia parts for cementless prostheses no cement pockets are provided, but instead the tibia part is provided at the lower side facing the tibia with a material coating which furthers the growing in of the bone, for example with porous titanium. This can take place in the manufacturing technology in such a manner that the tibia part for cementless applications can be won from tibia parts for cemented applications in such a manner that the cement pockets are filled with porous titanium.

The method in accordance with the invention for implanting a knee joint prosthesis comprises the following steps:

Selection of a suitable prosthesis type;
Resection of the tibia and of the femur in accordance with a predetermined execution of the cutting;
Selection of a tibia part from the kit in accordance with the invention;
Fixing the tibia part to the tibia;
Selection of a femur part from the kit which is suitable for this prosthesis type;
Fixing the femur part at the femur;
Selection of a bearing body from the kit which is suitable for the prosthesis type;
Insertion and where appropriate fixing of the bearing body.

The orthopedist can, after the selection of the suitable prosthesis type and resection of the tibia in accordance with a predetermined execution of the cutting, which is the same for all tibia parts, select a tibia part, fix the latter to the tibia, then select a corresponding femur part, fix the latter at the femur and finally select a suitable bearing body and insert it. Should it turn out during the operation that as a result of the anatomical conditions another prosthesis type is indicated instead, then the orthopedist can still intra-operatively decide on another type of knee joint prosthesis. In tibia parts for fixed bearing bodies he still has e.g. the choice between a bearing body with normal or particularly high congruence; in tibia parts for slidingly displaceably journalled and/or rotatably journalled bearing bodies he still has the choice among an entire spectrum of prosthesis types. This will be described in detail below.

In the method in accordance with the invention for the revision of a knee joint prosthesis with the help of a kit in accordance with the invention the following steps are carried out:

Decision whether the same prosthesis type is retained or a change is made to another prosthesis type;
Selection of a bearing body from the kit which is suitable for the selected prosthesis type;
Insertion and where appropriate fixing of the bearing body while retaining the original tibia part and/or the original femur part.

The orthopedist can thus first decide whether as a result of the anatomical conditions the same prosthesis type is retained or another prosthesis type should be used. The latter is clearly the more frequent case in revisions. Then the orthopedist can decide whether for the new prosthesis type the original femur part and/or the original tibia part can be retained, which depends among other things on the prosthesis type on which the orthopedist decides during the revision. Then the orthopedist can select from the kit in accordance with the invention a bearing body which is suitable for the selected prosthesis type and then insert the new tibia part or the new femur part or else—in the event that the tibia part and the femur part are retained—insert only the new bearing body.

In the following the invention will be explained in more detail both in regard to the apparatus and in regard to the method with reference to the drawings and with reference to exemplary embodiments.

BRIEF DESCRIPTION OF THE DRAWINGS

FIG. 8 illustrates a third type (type "PS") of a knee joint prosthesis with a tibia part in accordance with the invention, FIG. 9 illustrates a fourth type (type "SC") of a knee joint prosthesis with a tibia part in accordance with the invention.

DETAILED DESCRIPTION OF SPECIFIC EXEMPLARY EMBODIMENTS

Figure 1:
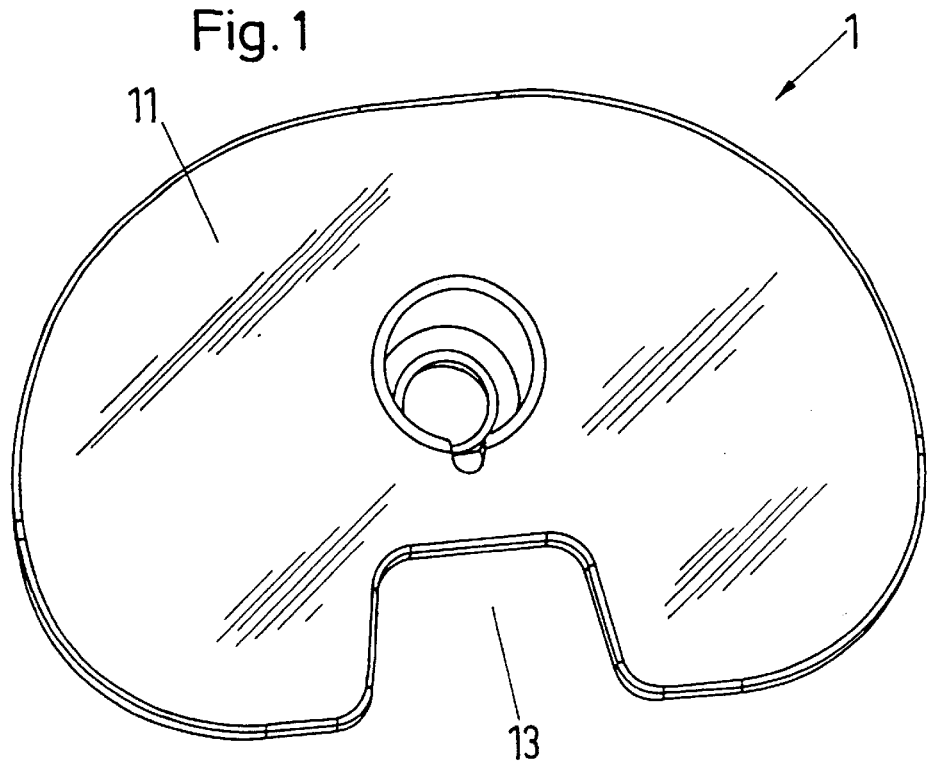
FIG. 1 is a plan view of a first exemplary embodiment of the tibia part in accordance with the invention.
Figure 2:
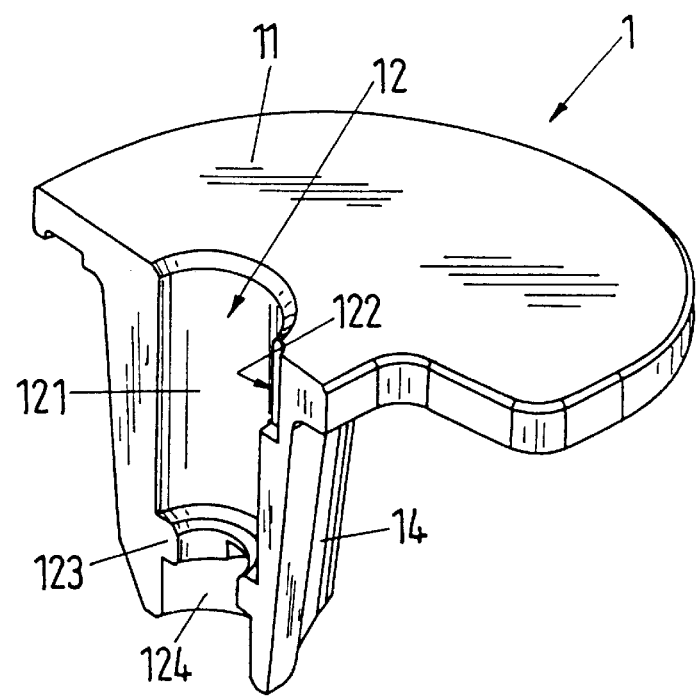
FIG. 2 is a perspective longitudinal section through the first exemplary embodiment of the tibia part in accordance with the invention.
Figure 3:
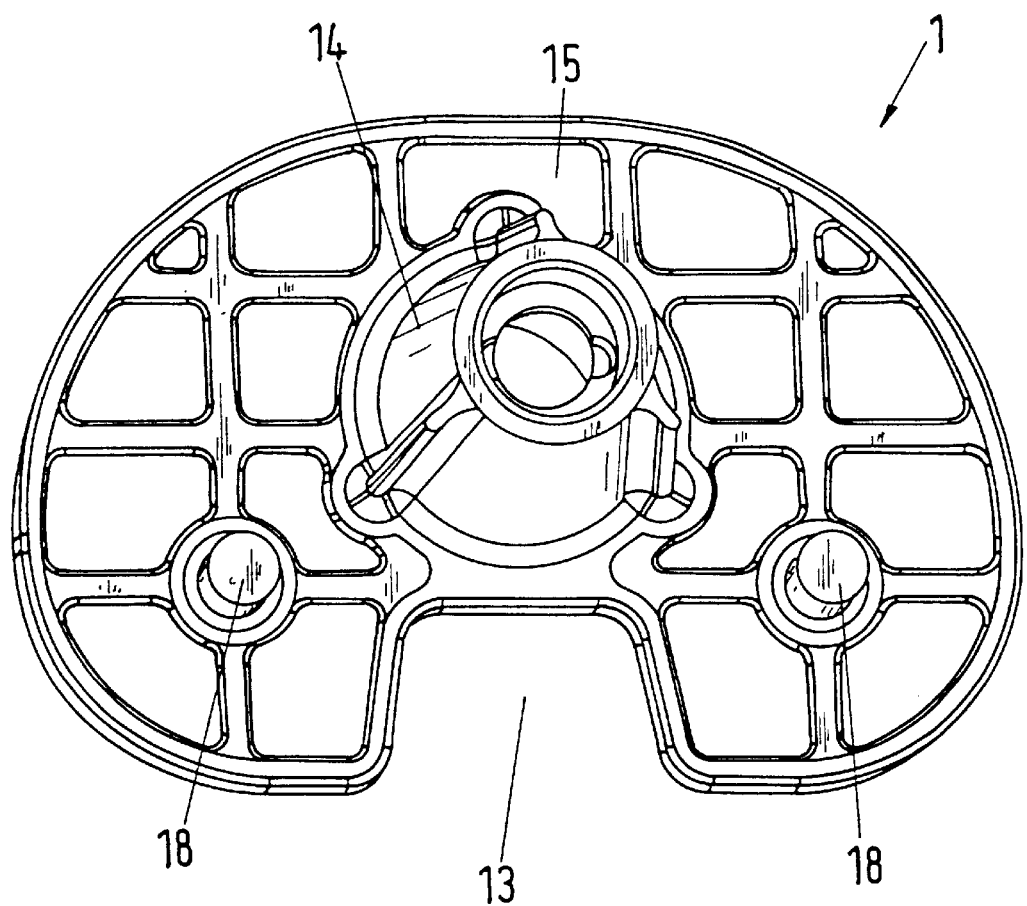
FIG. 3 is a view of the lower side of the first exemplary embodiment of the tibia part in accordance with the invention.

In FIGS. 1–3 a first exemplary embodiment of a tibia part in accordance with the invention for a knee joint prosthesis is illustrated, which is designated in its entirety with the reference symbol 1. FIG. 1 shows the tibia part 1 in a plan view; in FIG. 2 a perspective longitudinal section along the longitudinal axis of the tibia part 1 is illustrated; and FIG. 3 shows a plan view of the lower side of the tibia part 1, which faces the tibia in the normal position of use.

The tibia part 1 has a tibia bearing surface 11 for supporting a bearing body 2 (see FIGS. 6–9) and a bore 12 for the reception of a guiding element 3 (see FIGS. 6–9). A cut-out 13 for the rear cruciate ligament is provided at the posterior edge of the tibia bearing surface 11. Through this the tibia part 1 is suitable both for prosthesis types in which the rear cruciate ligament remains present and for those in which the rear cruciate ligament is no longer present or is no longer capable of functioning. The tibia part 1 furthermore has an extension piece 14 which extends substantially in the direction of the longitudinal axis and which serves for securing the tibia part 1 in the tibia.

This first exemplary embodiment is in particular suitable for prosthesis types in which the bearing body 2 is movably journalled relative to the tibia part 1. The bore 12 extends from the tibia bearing surface 11 and passes through the extension piece 14 and is designed in such a manner that it, depending on the design of the guiding element 3, can receive the latter either rotationally fixedly relative to the tibia part 1 or rotatably relative to the tibia part 1. For this the bore 12 comprises in this exemplary embodiment an upper region which adjoins at the tibia bearing surface 11 and which is composed of a cylindrical part 121 and a groove-like cut-out 122 which adjoins laterally thereto. If now the region of the guiding element 3 which engages into the bore 12 is formed to be substantially circularly cylindrical or conical, then the guiding element 3 is rotatable relative to the tibia part 1. If on the contrary the guiding element 3 has in its region which cooperates with the bore 12 a web or other projection in addition which engages into the groove-like cut-out 122, then the guiding element 3 is rotationally fixedly seated relative to the tibia part 1.

In the downward direction the upper region of the bore 12 is limited by a bulge-like ledge 123 which narrows the cross-section of the bore 12. Below the ledge 123 in the illustration the bore 12 ends with a cylindrical lower region 124 which serves for the reception of a separate anchoring shaft 16 (see FIG. 8 and FIG. 9) or a closure cap 17 (see FIG. 7) respectively. Depending on whether a separate anchoring shaft 16 is used or not, the closure cap 17 can also remain inserted; for this purpose it is preferably manufactured of a material, e.g. of polymethylmethacrylate (PMMA), which is compatible with the bone cement to be used. In order to connect the separate anchoring shaft 16 to the extension piece 14, the proximal end of the anchoring shaft 16 is introduced into the lower region 124 of the bore 12. Then from the tibia bearing surface 11 a waisted bolt is introduced into the bore 12 and is screwed into a thread which is provided in the end of the anchoring shaft 16. The waisted bolt is dimensioned in such a manner that after being screwed in its head lies in contact on the ledge 123, which serves as an abutment. In this way the extension piece 14 can be firmly connected to the separate anchoring shaft 16.

On the lower side, with which the tibia part 1 lies on the tibia, a plurality of cement pockets 15 are provided for receiving bone cement. In this embodiment the tibia part 1 is suitable for uses in which the tibia part 1 is fixed at the tibia by means of bone cement. The first exemplary embodiment of the tibia part 1 can however also be formed for cementless applications in a simple way. For this the lower side of the tibia part is provided with a material coating which furthers the growing in or the growing fast respectively of bone, for example with a coating of porous titanium. For the manufacture of a tibia part of this kind for cementless applications the cement pockets 15 of a tibia part for cemented applications can be filled up with porous titanium so that the material coating which furthers the growing in or the growing fast respectively of bone arises on the lower side of the tibia part 1.

With the exception of this material coating the tibia parts can be identically formed for cementless applications on the one hand and for applications with cement on the other hand. This is in particular advantageous in the manufacturing technology since the same tibia part can be produced for both kinds of uses, with it merely being necessary to perform one further processing step for cementless applications, namely the filling of the cement pockets with a suitable material.

On the lower side of the tibia part 1 one or more pins or pegs 18 can be provided in order to ensure a sure and correct placing of the tibia part 1 on the tibia and in order to prevent a rotating of the tibia part 1 relative to the tibia in particular during the implantation.

Figure 4:
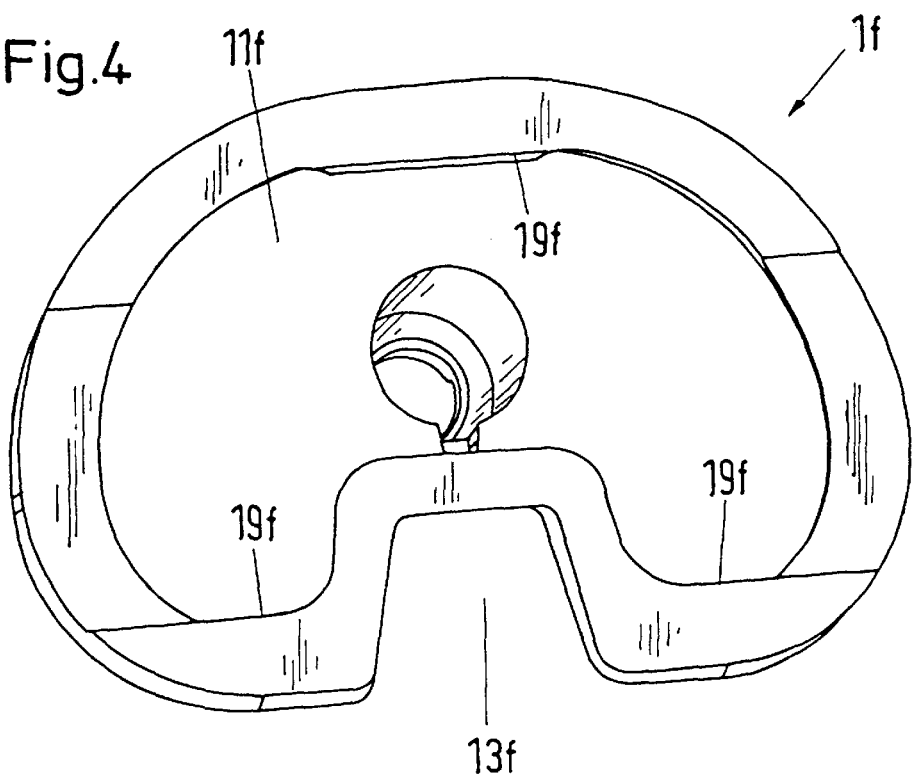
FIG. 4 is a plan view of a second exemplary embodiment of the tibia part in, accordance with the invention.
Figure 5:
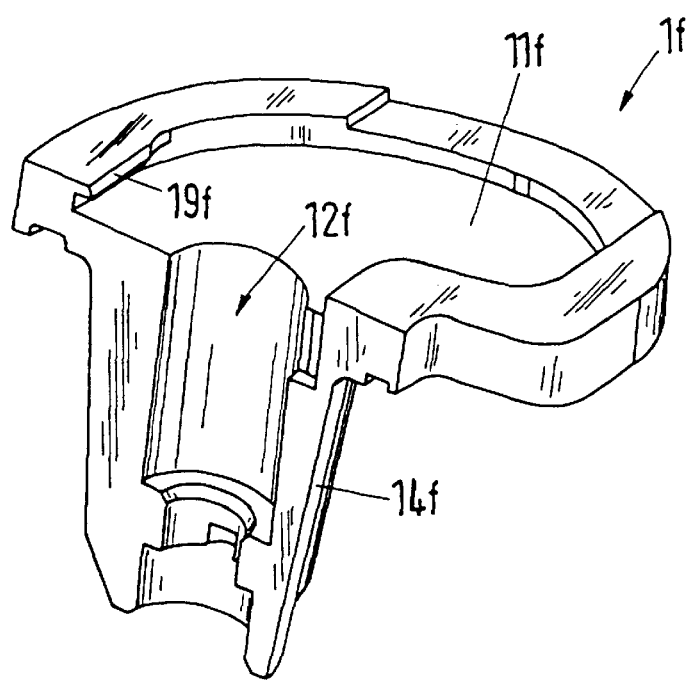
FIG. 5 is a perspective longitudinal section through the second exemplary embodiment of the tibia part in accordance with the invention.

In FIGS. 4 and 5 a second exemplary embodiment of a tibia part in accordance with the invention is illustrated which is suitable in particular for prosthesis types in which the bearing body is fixed, that is, immobile, relative to the tibia part. The parts corresponding to the exemplary embodiment in accordance with FIGS. 1–3 are in each case designated with the addition of an "f" (for "fixed"). FIG. 4 shows a perspective view of the tibia part 1f, whereas FIG. 5 shows a perspective longitudinal section through the tibia part 1f.

The second exemplary embodiment of the tibia part differs from the first one substantially only in that securing means are provided in the second exemplary embodiment in order to fix a suitably formed bearing body on the tibia bearing surface 11f. These securing means can for example be realized as projections 19f which cooperate with corresponding undercuttings at the bearing body, as has already been shown in the initially named specification EP-A-0,923, 916 (see in particular FIGS. 5–10). Otherwise the explanations with respect to the first exemplary embodiment, which was explained with reference to FIGS. 1–3, also hold in an analogous manner for the second exemplary embodiment in accordance with FIG. 4 and FIG. 5.

In FIGS. 6–9 four different types of knee joint prostheses are shown, which all contain the exemplary embodiment of the tibia part 1 in accordance with the invention which was explained with reference to FIGS. 1–3 and which can be put together from a kit of different parts, as will be explained in the following.

Figure 6:
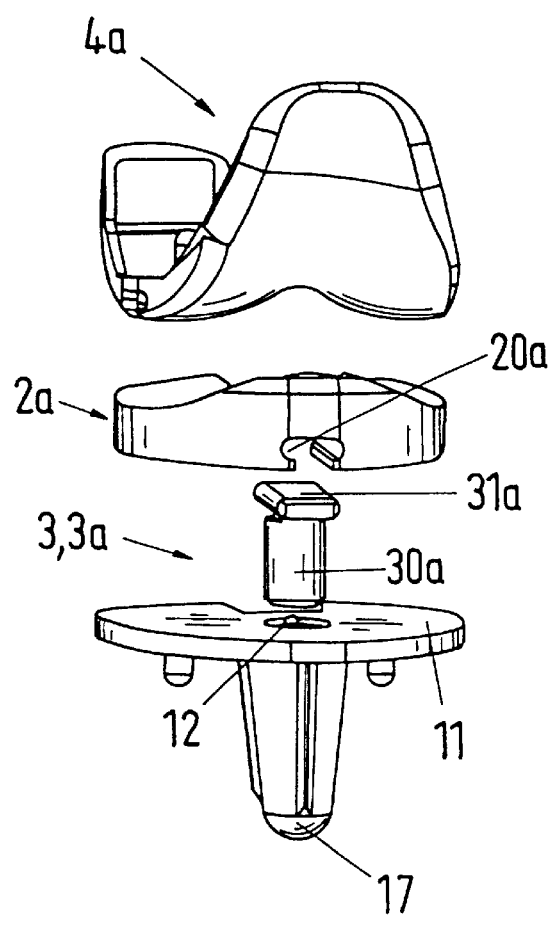
FIG. 6 illustrates a first type (type "CR") of a knee joint prosthesis with a tibia part in accordance with the invention.

In FIG. 6 a type of knee joint prosthesis is shown which is also designated as type "CR" (cruciate retaining). In this type of knee joint prosthesis the rear cruciate ligament of the patient is capable of functioning and can be retained; the collateral ligaments are likewise still capable of functioning and can be retained. The guiding element 3 is formed as a connecting rod 3a, the one end of which is formed as a circularly cylindrical pin 30a, which is rotatably journalled in the bore 12 of the tibia part 1 after introduction into the bore 12 of the tibia part 1. The other end 31a of the connecting rod 3a, which is formed in a web-like manner, engages into a groove 20a which is provided at the lower side of the bearing body 2a. Furthermore, one also recognizes in FIG. 6 a femur part 4a, which is however known per se.

In the type of knee joint prosthesis which is shown in FIG. 6 the bearing body 2a is, relative to the tibia part 1, rotationally displaceable on the bearing surface 11 of the tibia part 1 and also slidingly displaceable along the web 31a of the connecting rod 3a in the anterior and posterior direction respectively. This relatively great freedom of the knee joint prosthesis however presupposes, as already mentioned, that the rear cruciate ligament and the collateral ligaments of the patient are still capable of functioning and can be retained.

Figure 7:
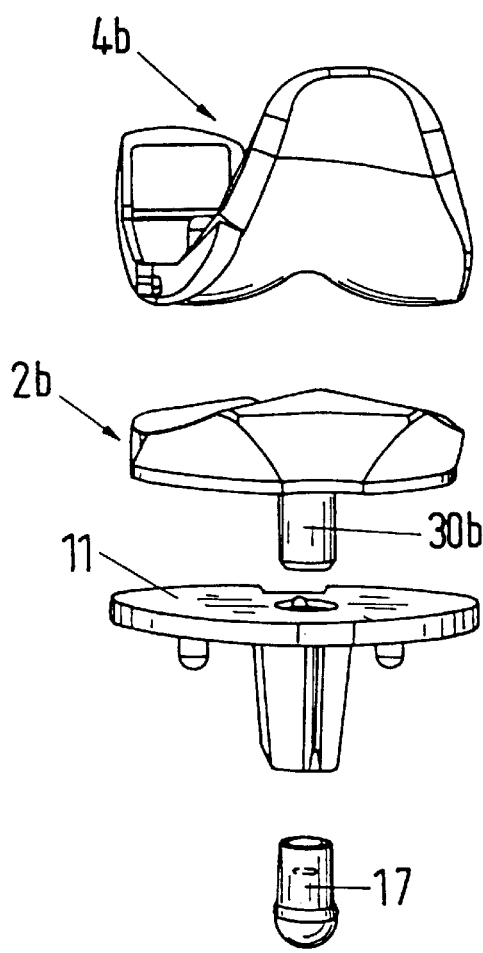
FIG. 7 illustrates a second type (type "UCOR") of a knee joint prosthesis with a tibia part in accordance with the invention.

In FIG. 7 a further type of knee joint prosthesis is shown, which is also designated as type "UCOR" (ultra congruent only rotating). This type of knee joint prosthesis is intended primarily for patients in whom the rear cruciate ligament is no longer present or is no longer capable of functioning, in whom however the collateral ligaments are still capable of functioning. It thus represents in a certain way an alternative to the type "PS", which will still be explained in more detail with reference to FIG. 8.

In the type "UCOR" in accordance with FIG. 7 the guiding element 3 is formed as a pin 30b which is either directly molded on at the bearing body 2b (is thus a constituent of the bearing body) or else is fixed to the latter. The pin 30b is circular cylindrically formed so that it is rotatably journalled in the bore 12 of the tibia part 1 after being introduced into the bore 12 of the tibia part 1. Thus the entire bearing body 2b is rotatable on the tibia bearing surface 11 relative to the tibia part 1, but however rotatable only. The femur part is thereby at best slidingly displaceable relative to the tibia part 1 to a very low extent (namely in positions in which the condyles of the femur part and the bearing shells of the bearing body are not precisely congruent). In all, the bearing shells of the bearing body 2b have a particularly high congruence with the condyles of the femur part 4b, which on the one hand leads to a good guiding and as a result of the large contact surface between the bearing shells of the bearing body 2b and the condyles of the femur part 4b to a comparatively low surface pressing. Moreover, the bearing shells of the bearing body 2b, which cooperate with the condyles of the femur part, are also drawn somewhat further upwardly in the posterior region, which reduces the risk of luxation, which is increased due to the lacking rear cruciate ligament.

In FIG. 8 a further type of knee joint prosthesis is shown, which is also designated as type "PS" (posterior stabilized). This type of knee joint prosthesis is intended primarily for patients in whom the rear cruciate ligament is no longer present or no longer capable of functioning, but in whom the collateral ligaments are very sound, however (that is, similarly as in the type "UCOR"). Both in the type "PS" and in the type of knee joint prosthesis which is to be explained later in more detail with reference to FIG. 9, a femur part 4c which is still to be explained in more detail is however also a constituent of the prosthesis. This femur part, which is still to be explained, can in principle also be used for the types of knee joint prosthesis in accordance with FIG. 6 and FIG. 7 (types "CR" and "UCOR"), but requires however that somewhat more bone material be removed from the femur bone, as will be explained more precisely later.

In the type "PS" of knee joint prosthesis, which is shown in FIG. 8, and which will also be explained in the following with the help of FIGS. 10–13, the bearing body 2c has a through-going elongate hole 20c. Passing through this elongate hole 20c there extends the guiding element 3c, the one end of which is designed as a circularly cylindrical pin 30c. This pin 30c is rotatably journalled after its introduction into the bore 12 in the tibia part 1. The other end 31c of the guiding element 3c protrudes in between the condyles of the femur part 4c and has a guiding surface 310c (see FIG. 10) which cooperates with a stabilizing element in the femur part 4c.

Figure 10:
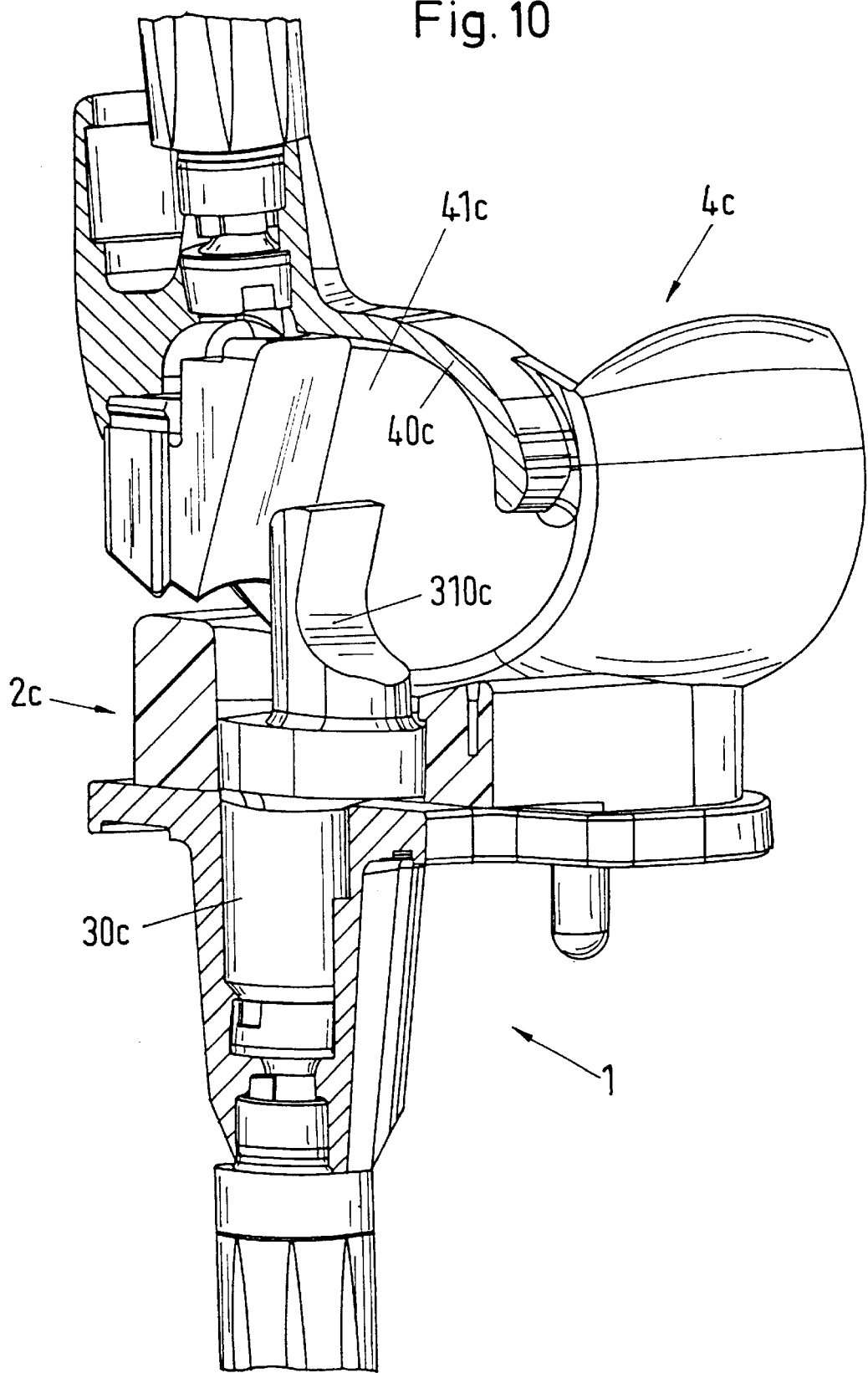
FIG. 10 illustrates the third type (type "PS") of the assembled knee joint prosthesis in a perspective illustration, in the state of extension.
Figure 11:
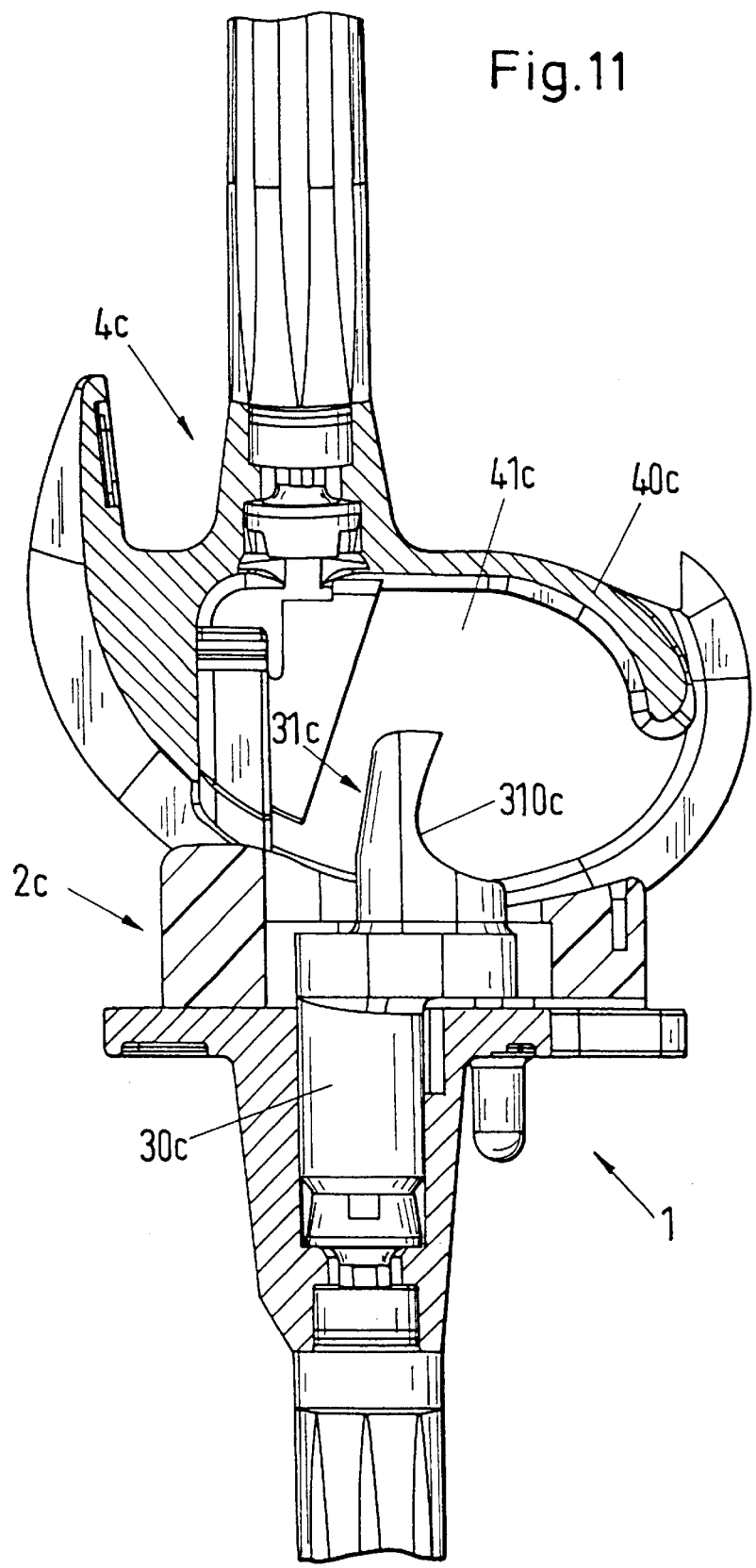
FIG. 11 illustrates the knee joint prosthesis in accordance with FIG. 10 in the state of extension, in a longitudinal section and in a side view.

This stabilizing element is here a connection web 40c which is formed in the manner of a wall and which together with the two side walls 41c, of which only one is illustrated in FIG. 10, defines a box into which the end 31c of the guiding element 3c protrudes. In FIG. 10 the type "PS" of the knee joint prosthesis is shown in perspective illustration in the state of extension (stretching); in FIG. 11 the state of extension is likewise illustrated, however in a longitudinal section and in a side view. In the state of extension the connection web 40c is not in engagement with the guiding surface 310c of the guiding element 3c.

Figure 12:
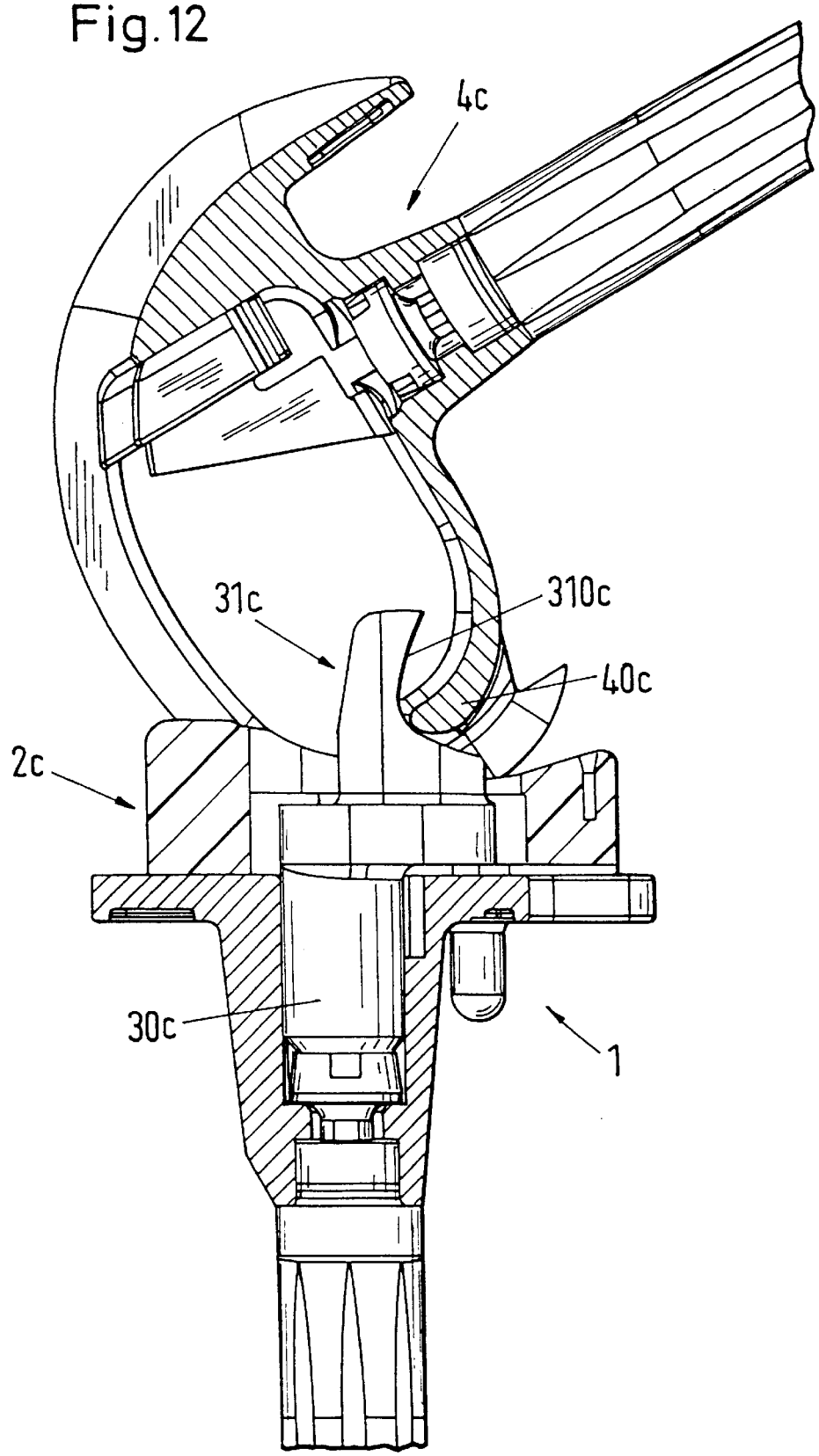
FIG. 12 illustrates the knee joint prosthesis in accordance with FIG. 10 in the state of flexion, in a longitudinal section and in a side view.
Figure 13:
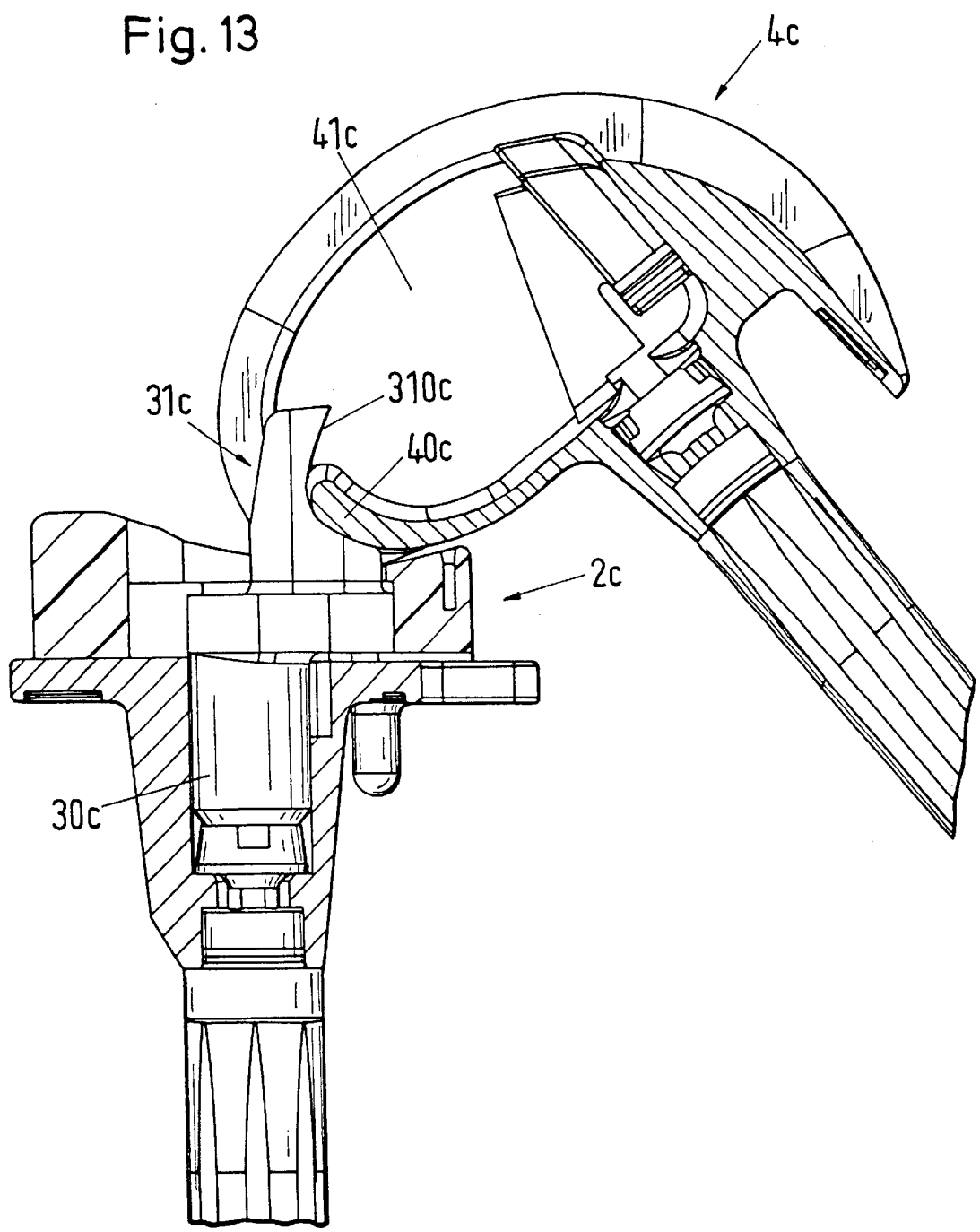
FIG. 13 illustrates the knee joint prosthesis in accordance with FIG. 10 in the state of maximum flexion, in a longitudinal section and in a side view.

If now a flexion of the knee takes place, then from a specific flexion angle—see FIG. 12—the outer wall of the connection web 40c which is formed in the manner of a wall comes into engagement with the guiding surface 310c of the guiding element 3c. The femur part 4c is thereby protected in the further flexion from sliding in the anterior direction, which would otherwise be possible as a result of the lacking rear cruciate ligament; it is also stabilized in the posterior position. This stabilizing in the posterior position then takes place up to the state of maximum flexion, which is illustrated in FIG. 13, with the bearing body 2c not being illustrated here in the posterior position, in which it is in reality located on maximal flexion, for reasons of drafting.

In FIG. 9 a further type of knee joint prosthesis is shown, which is also designated as type "SC" (semi constrained). This type of knee joint prosthesis is primarily intended for patients in whom neither the rear cruciate ligament nor the collateral ligaments are present or, respectively, in whom all these ligaments are no longer capable of functioning. The femur part 4d of this type agrees completely in this type of knee joint prosthesis with the femur part 4c which was described above with reference to FIG. 8 and FIGS. 10–13; thus one and the same femur part can be used for both types of knee joint prosthesis. This aspect of the invention is in principle self-reliant and independent of the use of a universal tibia part.

In the type "SC" in accordance with FIG. 9 the guiding element 3d is two-pieced and has a guiding piece 30d and a coupling piece 31d. The coupling piece 31d is insertable into a bore 300d of the guiding piece and is rotatably journalled in this bore 300d after being inserted into this bore 300d. The one end of the guiding piece 30d is formed as a pin 301d which is rotationally fixedly arranged after being inserted into the bore 12 of the tibia part 1. Thus whereas the coupling piece 31d is rotatably journalled in the bore 300d of the guiding piece 30d, the guiding piece 30d is rotationally fixedly arranged in the bore 12 of the tibia part 1.

For this purpose the pin 301d of the guiding piece 30d is provided with a projection or a fin 302d (FIG. 15) which reaches, after the introduction of the pin 301d into the bore 12 of the tibia part, into the groove-like cut-out 122 (see FIG. 2) of the bore 12 of the tibia part 1.

The bearing body 2d of this type of knee joint prosthesis corresponds to the bearing body 2c of the above-explained exemplary embodiment (see FIG. 8 and FIGS. 10–13 respectively). The guiding piece 30d has furthermore an end 303d which is formed in the manner of a web and which engages into the elongate hole 20d of the bearing body 2d. Since now the guiding piece 30d is however rotationally fixedly seated in the bore 12 of the tibia part 1, the bearing body 2 is also rotationally fixedly arranged relative to the tibia part 1.

Figure 14:
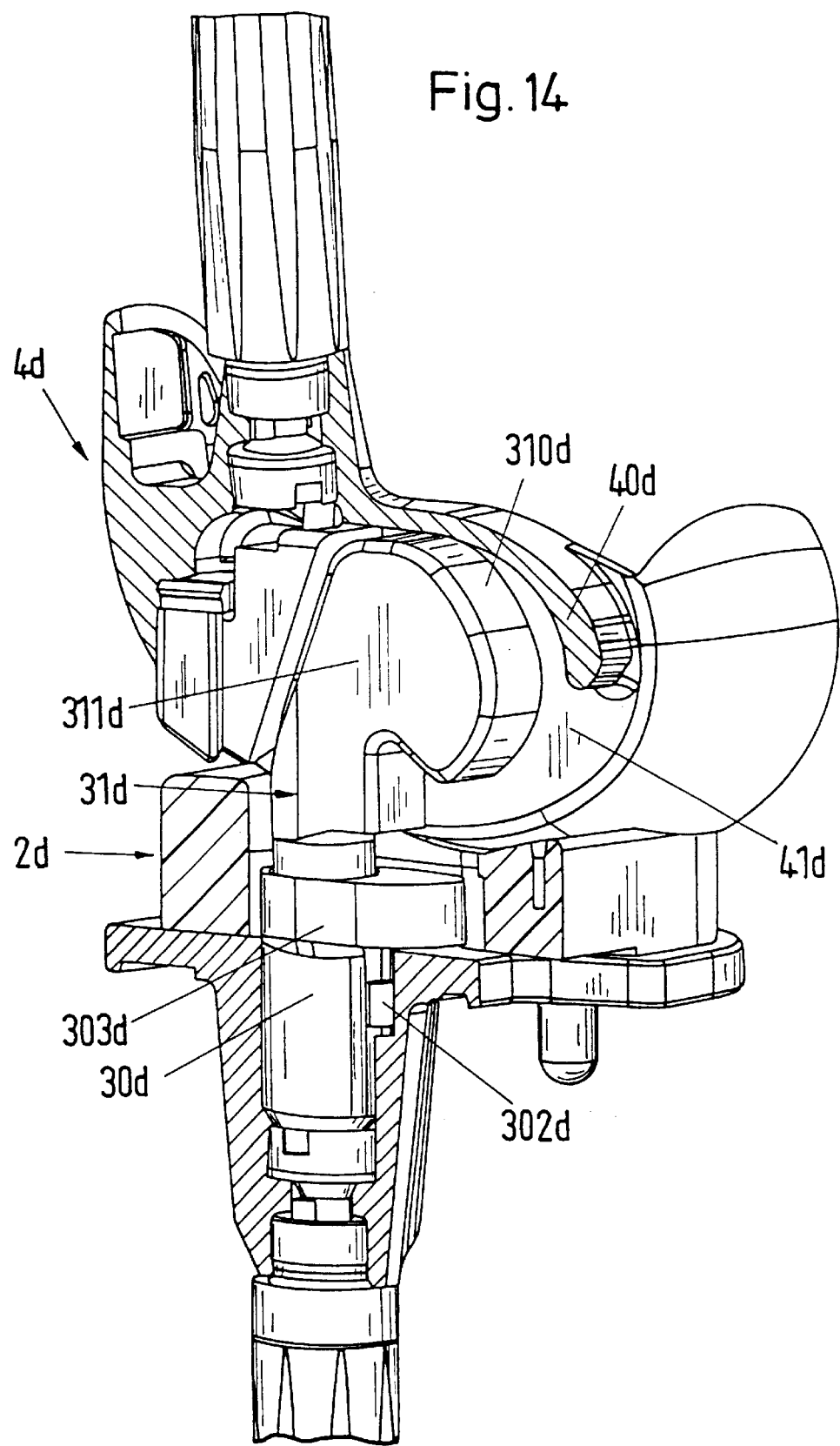
FIG. 14 illustrates the fourth type (type "SC") of the assembled knee joint prosthesis in a perspective illustration, in the state of extension.

The type "SC" of the prosthesis, which has already been shown in an exploded illustration in FIG. 9, will be explained in the following in more detail with the help of FIGS. 14–17. In this, FIG. 14 shows in a perspective view this type of knee joint prosthesis assembled and in the state of extension. One recognizes the wall-like connection web 40d of the femur part 4d, which together with the side walls 41d again forms a box, completely analogously to the above-described exemplary embodiment (indeed, the femur part is the same).

Figure 15:
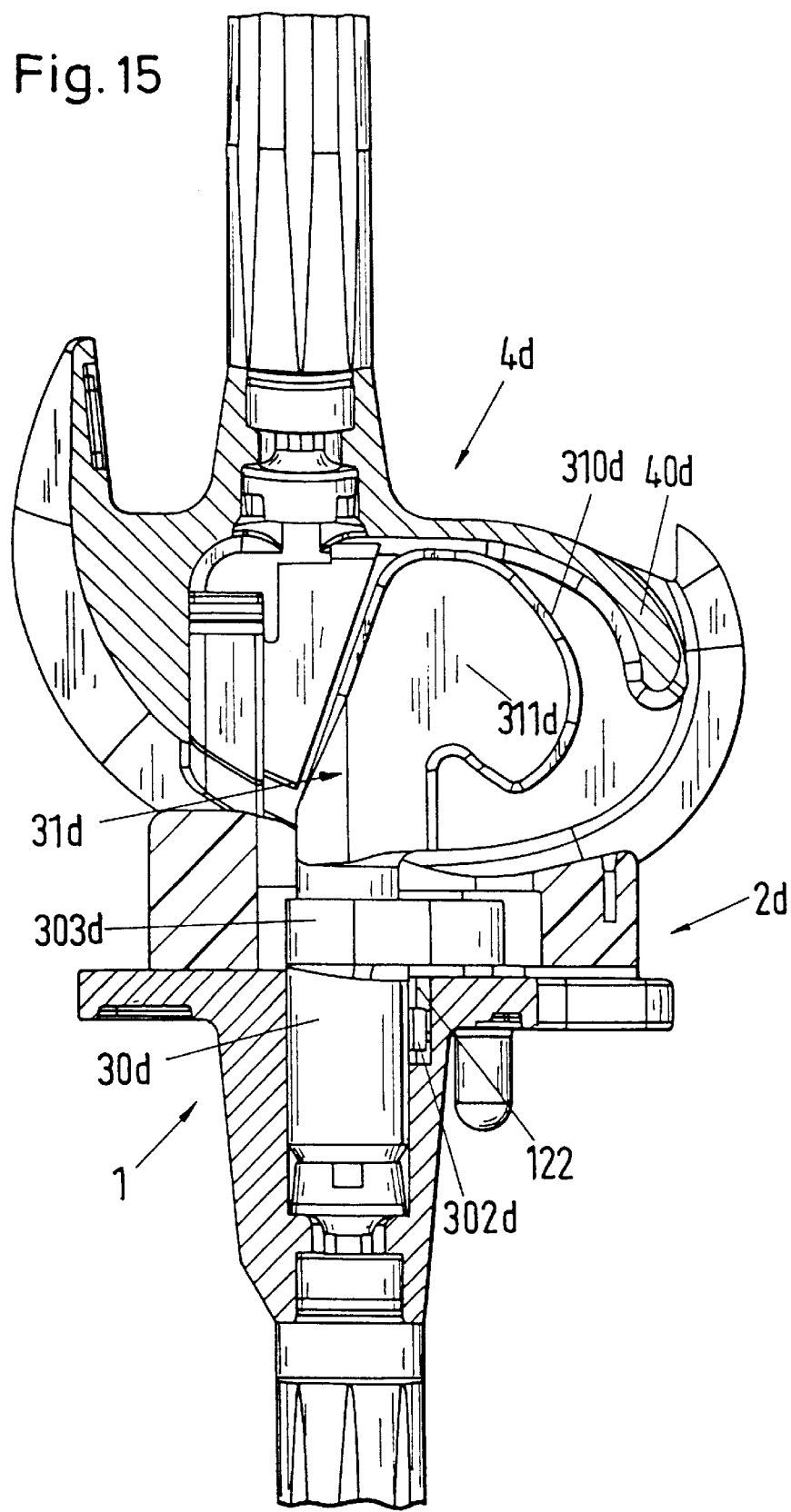
FIG. 15 illustrates the knee joint prosthesis in accordance with FIG. 14 in the state of extension, in a longitudinal section and in a side view.
Figure 16:
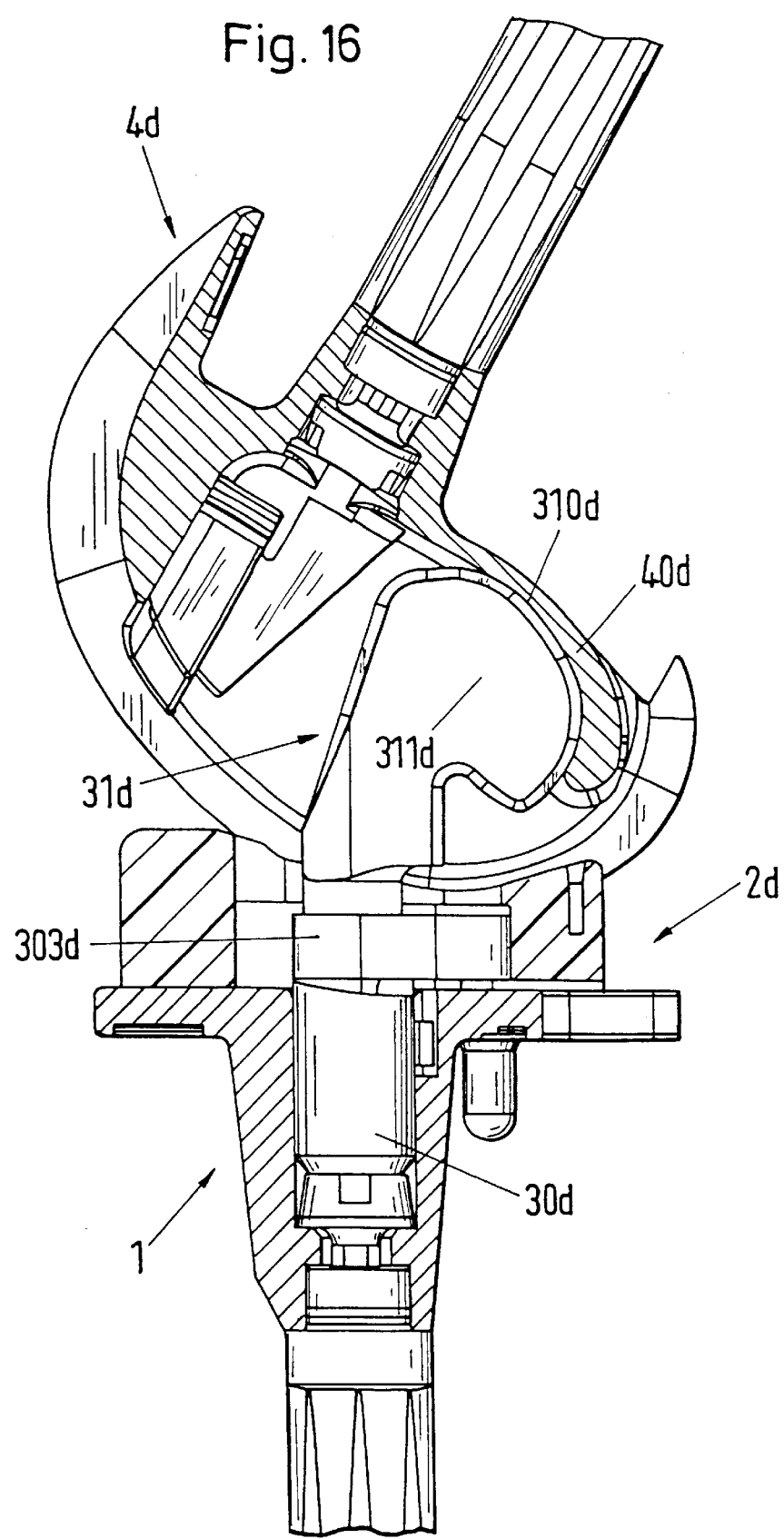
FIG. 16 illustrates the knee joint prosthesis in accordance with FIG. 14 in the state of flexion, in a longitudinal section and in a side view.
Figure 17:
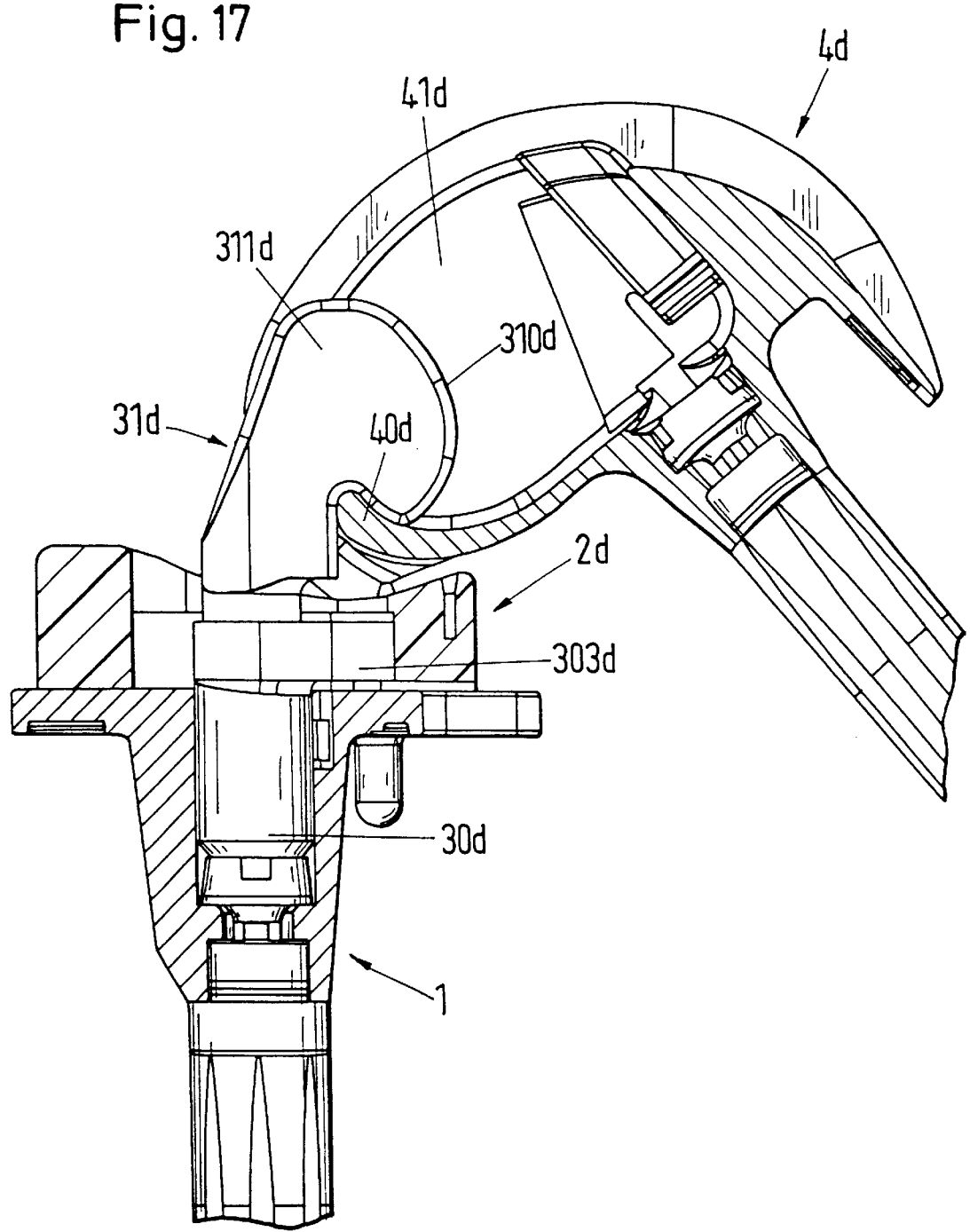
FIG. 17 illustrates the knee joint prosthesis in accordance with FIG. 14 in the state of maximum flexion, in a longitudinal section and in a side view.

An essential difference from the type "PS" consists in the type "SC" in that the guiding surface 310d of the guiding piece 31d comes into engagement not with the outer wall, but rather with the inner wall of the wall-like connection web 40d during the flexion. This is however not yet the case in the state of extension, as is shown in FIG. 14 and FIG. 15. In a slight flexion however the inner wall of the wall-like connection web 40d comes into engagement with the guiding surface 310d of the guiding piece 31d, as can be well recognized in FIG. 16, and remains so even up to the state of maximum flexion, which is illustrated in FIG. 17. In this it should again be remarked that both in FIG. 16 (slight flexion) and in FIG. 17 (maximum flexion) the bearing body 2d would in reality be located further to the posterior than is illustrated for drafting reasons in the relevant figures.

A further substantial difference is that the coupling piece 31d has two lateral stabilizing surfaces 311d, of which only one can be recognized in each case in FIGS. 14–17. These stabilizing surfaces serve for the varus/valgus stabilization and come into engagement in a corresponding lateral tilting of the prosthesis with the respective side wall 41d and thus prevent a lateral tilting of the femur part.

Therefore, this prosthesis no longer has very many degrees of freedom. The movement is guided to the greatest extent. The prosthesis however still permits a rotation of the femur part 4d relative to the bearing body 2d to a certain extent. However it is to be considered that this prosthesis type is of course intended primarily for patients in which both the rear cruciate ligament and the collateral ligaments are no longer capable of functioning or are no longer present respectively. The articulation movement must therefore necessarily be strongly guided.

Figure 18:
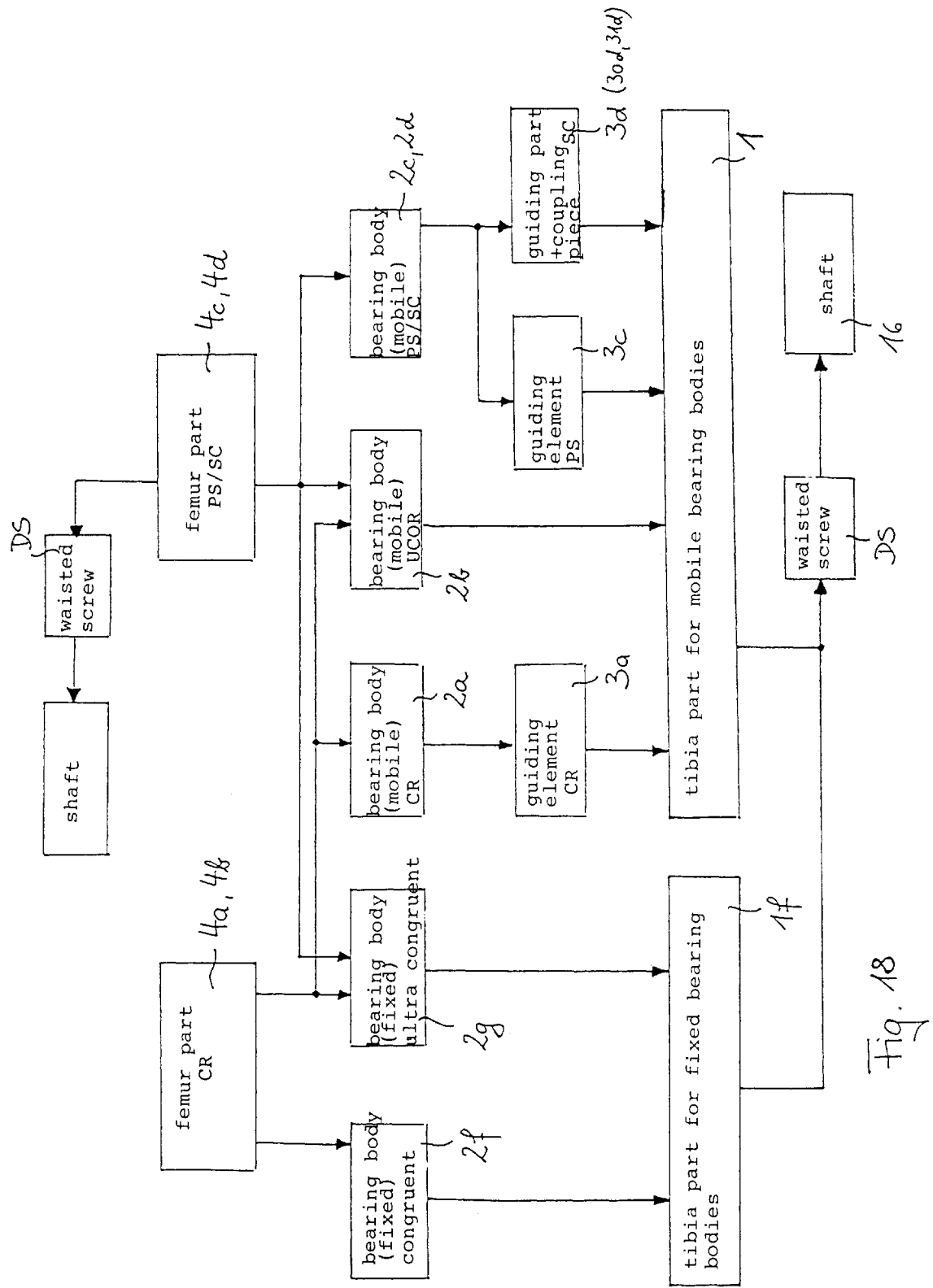
FIG. 18 illustrates a survey of combination possibilities of a kit which comprises tibia parts in accordance with the invention.

In FIG. 18, finally, a survey is illustrated which shows the large number of combination possibilities which are practically still available to the orthopedist during the operation. In this it is to be taken into consideration that in the preparation of the tibia, the execution of the cutting during the resection of the tibia is practically independent of the type of the knee joint prosthesis. In the preparation of the femur this is similar: The execution of the cutting during the resection is practically the same for both kinds of femur parts 4a, 4b and 4c, 4d respectively; however in the case in which a femur part 4c, 4d with a box is to be used, the femur must then still be cut out for the accommodation of the box. This facilitates for the orthopedist the preparation of the femur and the tibia and at the same time gives him the possibility of still reacting to the anatomical conditions during the operation and of being able to implant the respective ideal prosthesis type.

In the survey in FIG. 18 one recognizes the two types of tibia parts, namely the tibia parts 1 for displaceable and/or rotatable bearing bodies 2a, 2b, 2c, 2d on the one hand and the tibia parts 1a for fixed bearing bodies 2f and 2f on the other hand. The bearing bodies 2g correspond to the "UCOR" bearing bodies for displaceable or rotatable bearing bodies, but are firmly connected to the tibia part 1a however.

Furthermore, one recognizes in FIG. 18 the different bearing bodies 2, namely the displaceable and/or rotatable bearing bodies 2a, 2b, 2c, 2d on the one hand and the fixable bearing bodies 2f and 2g on the other hand. Moreover, one recognizes among the displaceable and/or rotatable bearing bodies the different guiding elements 3a, 3c, 3d, in the case of the guiding element 3d the guiding piece 30d and the coupling piece 31d.

Finally, one still recognizes the two types of femur parts, namely the types 4a, 4b without a box on the one hand and the types 4c, 4d with a box on the other hand. Depending on the state of the tibia a separate shaft can still be connected to the respective tibia part 1, 1a with the help of a waisted screw DS. The corresponding holds for the femur: Depending on the state a separate shaft 5 can still be connected to the respective femur part, with it being self-evident in both cases (tibia and femur) that the shaft is present in different sizes.

This naturally also holds for the remaining parts: In order to have a complete kit present, the individual parts must be completely present in the respective size. In practice, however, the number of parts which must actually be present in the operating room is very much more restricted, since the size of the prosthesis is of course already determined in the preoperative planning. It should thus be fully sufficient when in addition to the determined size in each case the next larger and the next smaller sizes of the individual parts are also present in the operating room in order to have available the full spectrum of all combination possibilities. After the operation the kit need only be refilled again and all possibilities are again available during the next implantation.

Even though it is clear that the combination possibilities are a maximum when all individual parts which are presented in FIG. 18 are present during an operation, it is however clear that kits can also be provided which cover only a portion of all possibilities. For example the orthopedist can determine from the beginning whether he wishes to use a displaceable and/or rotatable bearing body, or whether he wishes to implant with or without cement, etc. As a result of this the kit will then in each case be only a subset of the total kit.

What is claimed is:

1. A knee joint prosthesis kit adapted to change a mode of operation of a knee joint, the kit comprising a tibia part and a plurality of different guiding elements including at least one configured to be rotationally fixed relative to the tibia part and at least one configured to be rotatable relative to the tibia part; the tibia part having a bearing surface for supporting a bearing body and a bore for receiving any one of said guiding elements whereby the bore is configured to optionally mount the selected guiding element therein so that the guiding element is either rotationally fixed or rotatable relative to the tibia part, wherein each selected guiding element, when combined with the tibia part, is designed to provide the knee joint prosthesis with a different mode of operation depending on the selected guiding element.

2. A knee joint prosthesis kit in accordance with claim 1 further comprising an extension piece for securing the tibia part to the tibia, an anchoring shaft for the tibia part, and a connector for firmly connecting the extension piece to the anchoring shaft.

3. A knee joint prosthesis kit in accordance with claim 1, including means securing the bearing body on the tibia bearing surface.

4. A knee joint prosthesis kit adapted to change a mode of operation of a knee joint, the kit comprising at least one tibia part having a tibia bearing surface, a plurality of different guiding elements including at least one configured to be rotationally fixed relative to the tibia part and at least one configured to be rotatable relative to the tibia part, at least one bearing body to be supported on the tibia bearing surface, the at least one bearing body including bearing shells on a side that faces away from the tibia bearing surface, at least one femur part including condyles for cooperating with the bearing shells of the bearing body, the tibia part including a bore for receiving any one of the guiding elements, the bore being configured to optionally receive a selected guiding element therein so that the guiding element is either rotationally fixed or rotatable relative to the tibia part.

5. A knee joint prosthesis kit in accordance with claim 4 at least one tibia part and at least one bearing body define means for fixing the bearing body at the tibia bearing surface.

6. A knee joint prosthesis kit in accordance with claim 5 wherein at least one bearing body includes a bearing slidingly displaceably mounting the bearing body on the tibia bearing surface, and wherein at least one of the guiding elements includes a connecting rod having one end rotatably journalled in the bore of the tibia part and a guiding section which cooperates with the bearing body and permits displacement of the bearing body relative to the tibia bearing surface in anterior and posterior directions.

7. A knee joint prosthesis kit in accordance with claim 4 wherein at least one bearing body has a fixed guiding element on its side facing the tibia bearing surface which rotatably journals the bearing body in the bore of the tibia part.

8. A knee joint prosthesis kit in accordance with claim 4 wherein the femur part includes a stabilizing element, wherein at least one bearing body has an axial through-going hole, and wherein at least one guiding element is provided which can be passed through the hole in the bearing body, one end of the guiding element forming a pin which extends into the bore in the tibia part and being rotatably journalled therein, another end of the guiding element protruding in between the condyles of the femur part and having a guiding surface cooperating with a stabilizing element of the femur part.

9. A knee joint prosthesis kit in accordance with claim 4 wherein the femur part includes a stabilizing element, wherein at least one guiding element includes a guiding piece which extends into the bore in the tibia part and which is formed so that it is rotationally fixed relative to the tibia part and the bearing body, and a coupling piece rotatably journalled in the guiding piece and having a stabilizing piece which reaches between the condyles of the femur part and includes a guiding surface cooperating with the stabilizing element of the femur part.

10. A knee joint prosthesis kit in accordance with claim 9 wherein the stabilizing element of the femur part comprises a connection web which cooperates with first and second side walls to form a box arranged between the condyles cooperating with one of a guiding surface of a guiding element and a stabilizing piece of the guiding element.

11. A method for implanting a knee joint prosthesis comprising preparing the knee joint for implanting the prosthesis, assembling an implant from an implant kit comprising at least one tibia part for the knee prosthesis, at least one femur part for the knee prosthesis, and a plurality of different guiding elements providing the knee prosthesis with a desired mode of operation, the guiding elements including at least one configured to be rotationally fixed relative to the tibia part and at least one configured to be rotatable relative to the tibia part, the tibia part including a tibia bearing surface for supporting a bearing body and a bore for receiving any one of the guiding elements, the bore being configured to optionally receive a selected guiding element therein so that the guiding element is either rotationally fixed or rotatable relative to the tibia part, determining the desired mode of operation for the knee prosthesis, selecting a guiding element which, upon implantation, provides the knee prosthesis with the desired mode of operation, inserting the selected guide element into the tibia part bore, and connecting the selected guiding element to the bearing body.

* * * * *